United States Patent [19]

Schubart et al.

[11] 3,998,841

[45] Dec. 21, 1976

[54] CHLOROTHIO-N-PHTHALIMIDE AND PROCESS THEREFOR

[75] Inventors: Rüdiger Schubart, Cologne; Manfred Blazejak, Duesseldorf; Ernst Roos, Odenthal-Osenau, all of Germany

[73] Assignee: Bayer Aktiengesellschaft, Leverkusen, Germany

[22] Filed: June 7, 1974

[21] Appl. No.: 477,546

[30] Foreign Application Priority Data

June 14, 1973 Germany .......................... 2330241

[52] U.S. Cl. ............................................. 260/326 S
[51] Int. Cl.$^2$ ...................................... C07D 209/34
[58] Field of Search ................... 260/326 S, 543 H

[56] References Cited

UNITED STATES PATENTS 3,360,542  12/1967  Kuhle et al. ................... 260/543 H

OTHER PUBLICATIONS

E. Kuhle, "Syn. Org. Chem." (1970) p. 564.

*Primary Examiner*—Lewis Gotts
*Assistant Examiner*—D. R. Phillips
*Attorney, Agent, or Firm*—Burgess, Dinklage & Sprung

[57] ABSTRACT

Chlorothio-N-phthalimide is prepared by reacting N,N'-dithio-bis-phthalimide with chlorine or a chloriating agent at a temperature of 20° to 100° C. The product of the process can be used as an intermediate for preparing vulcanization retarding agents. The product produced can also be utilized to prepare N-[2-formylpropylthio-(2)]-phthalimide by reaction with isobutyraldehyde in the presence of an acid binding agent.

1 Claim, No Drawings

CHLOROTHIO-N-PHTHALIMIDE AND PROCESS THEREFOR

BACKGROUND

This invention relates to chlorothio-N-phthalimide, a process for preparing it, and its use.

Chlorothio-N-phthalimide is a novel compound. According to Synthesis, 1969/1970, page 564, the sulphur bridge of N,N'-dithio-bis-phthalimide can neither be broken nor eliminated by means of chlorine under the usual conditions; chlorinated derivatives are obtained instead.

SUMMARY

It has been found that in contradiction to these statements, chlorolysis to yield the new chlorothio-N-phthalimide, will readily take place when N,N'-dithio-bis-phthalimide is reacted with chlorine or a chlorinating agent at a temperature in the region of 20° to 100° C.

The reaction is preferably carried out within the temperature range of about 30° to about 60° C.

N,N'-Dithio-bis-phthalimide is already known (Canadian Journal of Chemistry, Volume 44, page 2112 (1966)).

DESCRIPTION

The reaction may be illustrated by the following reaction scheme:

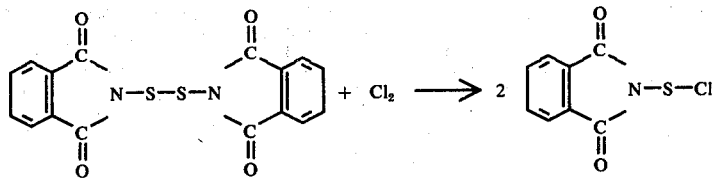

Other chlorinating agents may be used instead of chlorine, in particular sulphuryl chloride.

The reaction is generally carried out with stoichiometric quantities of N,N'-dithio-bis-phthalimide and chlorine or chlorinating agents although one or other of the starting materials may also be used in slight excess, in particular less than 10 mol % or Val %, i.e., % of equivalent weight.

The reaction may also be carried out in the presence of a solvent which is inert towards chlorine under the reaction conditions. The following are examples of such solvents: perhalogenated aliphatic hydrocarbons, in particular tetrachloromethane, aromatic hydrocarbons such as benzene and nitrobenzene and preferably aromatic hydrocarbons, in particular chlorobenzene and dichlorobenzene.

The reaction is generally carried out by suspending and/or dissolving N,N'-dithio-bis-phthalimide in the solvent and adding chlorine or the chlorinating agent whilst stirring. When all the chlorine or chlorinating agent has been added, the reaction mixture is left to react for some time and the solvent is then partly or completely distilled off, optionally under vacuum, and the reaction product is isolated. It may be advantageous to distill off only part of the solvent and subsequently to add a solvent which has a very low dissolving power for the chlorothio-N-phthalimide reaction product and which is miscible with the solvent used during the reaction. These solvents which are subsequently added may advantageously be conventional inert solvents which have not to be inert towards chlorine under the reaction conditions, e.g., aliphatic hydrocarbons and mixtures thereof such as petroleum ether or light petrol.

In this way, for example, the reaction product may be precipitated and may then advantageously be isolated from the reaction mixture or the solvent by a known method, such as filtration or centrifuging.

The reaction is normally performed at atmospheric pressure although reduced or elevated pressure may also be employed. In some cases, it may be particularly advantageous to employ an elevated pressure of up to about 10 excess atmospheres and in particular up to about 2 excess atmospheres so as to obtain a higher reaction velocity and a shorter reaction time.

The process according to the invention may, of course, also be carried out continuously, e.g., in a reaction tube, a cascade of reaction vessels or some other apparatus known for continuous processes.

Chlorothio-N-phthalimide is a new intermediate product which by virtue of its reactive group is suitable for producing various end products such as herbicidal compounds or auxiliary agents for rubbers.

It may be used with particular advantage for preparing N-[2-formylpropylthio-(2)]-phthalimide which has been disclosed as a vulcanization retarder in DOS No. 2,005,692. This may be carried out by reacting chlorothio-N-phthalimide with isobutyraldehyde in the presence of an acid binding agent.

This reaction may be carried out within a wide temperature range, preferably from 0° to 100° C and in particular from 20° to 40° C.

The acid binding agent used may be an inorganic or organic base.

The inorganic base used is preferably an oxide, hydroxide, carbonate, bicarbonate and a salt which is basic in reaction of organic acids, in particular the acetates, of alkali metals and alkaline earth metals. Sodium carbonate, potassium carbonate, calcium oxide, calcium hydroxide, calcium bicarbonate, calcium carbonate and sodium acetate are specific examples.

Among the organic bases used, aliphatic, araliphatic, aromatic and heterocyclic tertiary amines are particularly suitable. In these amines, the nitrogen may be substituted by various radicals, which may be the same or different. Aliphatically aromatically substituted amines and N-substituted heterocyclic compounds are examples of such bases. The choice of tertiary amines may advantageously be dictated by their accessibility. Dimethylbenzylamine and methyl- and dimethyl-pyridines are preferred, the pyridines preferably used as mixtures.

The quantity of the acid binding agent used depends upon the quantity of hydrogen chloride which is split off according to the stoichiometric relations of the reaction, as will be clear from the following reaction scheme:

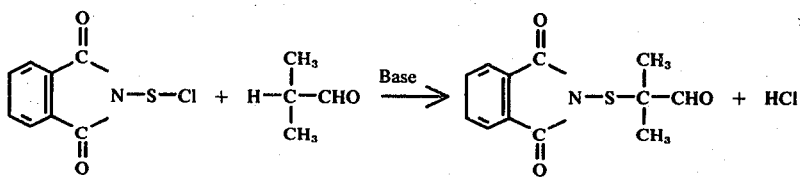

There is generally no harm in having an excess of acid binding agent. If it is a liquid, e.g., dimethylbenzylamine, it may serve as a solvent at the same time. In some cases, less than the equivalent quantity may be used, but the stoichiometric quantity is generally preferred.

The reaction may also be carried out in a solvent or a solvent mixture. The following are examples of suitable solvents: Aliphatic, cycloaliphatic and aromatic hydrocarbons such as petroleum ether, light petrol, cyclohexane, benzene, toluene and xylene. Aliphatic and aromatic chlorinated hydrocarbons may also be used, e.g., methylene chloride, chloroform, tetrachloromethane, chlorobenzene and dichlorobenzene. Aliphatic and heterocyclic ethers are also suitable, e.g., diethylether, diisopropylether, dioxane and tetrahydrofuran, although other solvents, such as nitrobenzene and acetonitrile, may also be used.

The end product N-[2-formylpropylthio-(2)]-phthalimide may be isolated by usual methods. For further purification, it may be advantageous to recrystallize the isolated product from an ester, in particular ethyl, propyl or butyl acetate.

According to a particularly advantageous method of carrying out the process of the invention, preparation of the starting material N,N'-dithio-bis-phthalimide, chloralysis of the starting material to produce chlorothio-N-phthalimide in accordance with the invention and the use of this compound according to the invention to produce N-[2-formylpropylthio-(2)]-phthalimide by reacting it with isobutyraldehyde are all carried out by a so-called one-pot process in which neither the starting material nor the reaction product of the process according to the invention are isolated. The following procedure may advantageously be employed:

Sulphur chloride is dissolved in a solvent, e.g., chlorobenzene, and then added to a suspension of phthalimide in the same solvent. The resulting N,N'-dithio-bis-phthalimide is not isolated but instead, the reaction solution is reacted with chlorine which may be added either in a gaseous or a liquid form, to produce chlorothio-N-phthalimide. Excess chlorine may be removed from the resulting reaction solution by sucking it off in a vacuum or blowing it out with an inert gas, e.g., nitrogen. The appropriate quantity of isobutyraldehyde used as the reactant is then added followed by the acid binding agent.

After termination of the reaction, the hydrochloric acid salt to which the acid binding agent has been converted in the course of the reaction is removed from the reaction mixture, e.g., by filtration or by washing out the organic reaction mixture with water. The reaction product, N-[2-formylpropylthio-(2)]-phthalimide, is then isolated from the organic reaction solution, e.g., by removal of the solvent by distillation under vacuum, precipitation by the addition of a solvent with a sufficiently low dissolving power and filtration.

The special advantage of this use according to the invention of chlorothio-N-phthalimide is that it saves labor because the intermediate compound is not isolated and also that the end product obtained is a N-[2-formylpropylthio-(2)]-phthalimide which, in contrast to the product obtained by the process according to DOS No. 2.005,692, is completely odorless, so does not require elaborate purification processes.

EXAMPLE 1

215 g (0.63 mol) of N,N'-dithio-bis-phthalimide are reacted with 43 g (0.61 mol) of chlorine in 1200 ml of chlorobenzene at 35° C while stirring, the chlorine being added as it is consumed. The reaction mixture is stirred for a further 60 minutes at the same temperature. The solvent is then drawn off under vacuum and the reaction mixture reduced to about one third of its volume. It is then filtered to remove slight traces of unreacted starting material. The reaction solution so obtained is then mixed with an equal volume of light petrol (boiling range from 60 to 95° C) and cooled to 10° C. The precipitated reaction product is filtered off and dried under vacuum. 219 g (85% of the theory) of chlorothio-N-phthalimide. are obtained as yellow crystals, melting point 135°–137° C.

EXAMPLE 2

(One pot process)

A solution of 70.5 g. (0.52 mol) of sulphur chloride and 70 ml of chlorobenzene is introduced dropwise into a suspension of 147 g (1 mol) of phthalimide (melting point 233°–234° C), 500 ml of chlorobenzene and 150 g of N,N-dimethylbenzylamino in the course of 1½ hours while stirring at a temperature of from 45° to 50° C. Stirring is continued at the same temperature for a further 2 hours and 37 g (0.52 mol) of chlorine are then introduced at about 40° C. When all the chlorine has been added, stirring is continued for a further 30 minutes at 40° C. The slight chlorine excess is then substantially removed under vacuum, and 75.5 g. (1.05 mol) of isobutyraldehyde (dried over sodium sulphate) are introduced dropwise with cooling at 30° to 35° C. Stirring is continued for 1 more hour at 30° C and the reaction mixture is then neutralized with N,N-dimethylbenzylamine at 20° to 25° C; this requires about 150 g. 750 ml of light petrol (boiling range 60° to 95° C) are then added and the reaction mixture is briefly stirred before 0.5 kg of ice are introduced. The reaction mixture rapidly cools to about −6° C. The temperature is then allowed to rise to about 0° C in the course of 1 hour. The precipitated reaction product is then filtered off and washed with water and then with a small quantity of light petrol. After drying under vacuum at 50° C, 212 g (85% of the theory) of N-[2-formylpropylthio-(2)]-phthalimide are obtained in the form of coarse, colorless and odorless crystals melting at 122° to 126° C.

EXAMPLE 3

(Use)

19 g (0.264 mol) of isobutyraldehyde are introduced dropwise into a mixture of 52 g (0.244 mol) of chlorothio-N-phthalimide and 250 ml of chlorobenzene at 30° to 35° C while stirring. When all the isobutyraldehyde has been added, stirring is continued for some time and 35 g (0.26 mol) of N,N-dimethylbenzylamine are added dropwise with cooling to about 20° C. The reaction mixture is then briefly stirred and left to cool to room temperature. The reaction solution is then washed two or three times with water and dried over sodium sulphate. It is then concentrated by evaporation under vacuum to about one third of its volume and an equal volume of light petrol (boiling range 60° to 95° C) is added to the warm solution which is then cooled to about 10° C. The precipitated reaction product is suction filtered and dried under vacuum. 54 g of crude product with a melting point of 122°–126° C are obtained. After recrystallization from ethyl acetate, N-[2-formylthiopropyl-(2)]-phthalimide melting at 129°–129.5° C are obtained in the form of coarse odorless crystals.

What is claimed is:
1. Chlorothio-N-phthalimide.

* * * * *